(12) United States Patent
Salmelainen

(10) Patent No.: US 8,933,417 B2
(45) Date of Patent: Jan. 13, 2015

(54) COMBINED LENS AND REFLECTOR, AND AN OPTICAL APPARATUS USING THE SAME

(75) Inventor: Pauli Salmelainen, Masku (FI)

(73) Assignee: Wallac Oy, Turku (FI)

( * ) Notice: Subject to any disclaimer, the term of this patent is extended or adjusted under 35 U.S.C. 154(b) by 712 days.

(21) Appl. No.: 13/145,666

(22) PCT Filed: Jan. 18, 2010

(86) PCT No.: PCT/FI2010/050024
§ 371 (c)(1),
(2), (4) Date: Sep. 9, 2011

(87) PCT Pub. No.: WO2010/084246
PCT Pub. Date: Jul. 29, 2010

(65) Prior Publication Data
US 2012/0043476 A1    Feb. 23, 2012

Related U.S. Application Data

(60) Provisional application No. 61/149,542, filed on Feb. 3, 2009.

(30) Foreign Application Priority Data

Jan. 26, 2009    (FI) ..................................... 20095065

(51) Int. Cl.
*G01N 21/64*    (2006.01)
*G02B 17/00*    (2006.01)
*G02B 17/08*    (2006.01)

(52) U.S. Cl.
CPC ............ *G02B 17/008* (2013.01); *G01N 21/645* (2013.01); *G02B 17/086* (2013.01)
USPC .............. 250/458.1; 250/339.06; 250/339.11; 250/341.8; 250/363.01; 250/365; 359/364; 359/365

(58) Field of Classification Search
CPC ... G01N 21/64; G01N 21/35; G01N 21/3563; G01N 21/3581; G01N 21/00
USPC ................ 250/339.06, 339.11, 341.8, 458.1, 250/363.01, 365; 359/364, 365
See application file for complete search history.

(56) References Cited

U.S. PATENT DOCUMENTS 2,683,394 A * 7/1954 Polanyi et al. ................ 359/729
4,227,079 A   10/1980 Dukes et al.
(Continued)

FOREIGN PATENT DOCUMENTS

CH          677439 A5    5/1991
GB       1 095 078 A    12/1967
(Continued)

OTHER PUBLICATIONS

Finnish Search Report, dated Oct. 26, 2009, from corresponding Finnish application.
(Continued)

*Primary Examiner* — David Porta
*Assistant Examiner* — Djura Malevic
(74) *Attorney, Agent, or Firm* — Young & Thompson

(57) ABSTRACT

A lens and reflector unit for optical measurements includes first and second convex surface sections of the lens and reflector unit. Both have their respective central normal lines. A first flat surface section has a normal direction that divides the angle between the central normal lines into equal halves. A third convex surface section has a third central normal line, and the fourth convex surface section has a fourth central normal line. A second flat surface section has a normal direction that divides the angle between the third and fourth central normal lines into to equal halves.

9 Claims, 5 Drawing Sheets

(56) References Cited

U.S. PATENT DOCUMENTS

| | | |
|---|---|---|
| 5,506,416 A | 4/1996 | Rizvi |
| 5,530,586 A | 6/1996 | Yasugaki |
| 5,682,449 A | 10/1997 | Taira-Griffin |
| 6,518,572 B1 | 2/2003 | Kishii et al. |
| 2004/0095573 A1* | 5/2004 | Tsai et al. ............... 356/237.5 |
| 2006/0124835 A1* | 6/2006 | Kiyomoto et al. ............ 250/216 |
| 2006/0158615 A1 | 7/2006 | Williamson |
| 2009/0310135 A1* | 12/2009 | Bockstaele et al. ........... 356/328 |

FOREIGN PATENT DOCUMENTS

| | | |
|---|---|---|
| JP | 8271209 A | 10/1996 |
| JP | 10221419 A | 8/1998 |
| JP | 2002 022606 A | 1/2002 |

OTHER PUBLICATIONS

International Search Report, dated Jul. 21, 2010, from corresponding PCT application.

* cited by examiner

COMBINED LENS AND REFLECTOR, AND AN OPTICAL APPARATUS USING THE SAME

FIELD OF THE INVENTION

The invention relates to a lens and reflector unit for controlling the propagation path of a beam of optical radiation, for example in an optical measurement instrument. An optical measurement can be, for example but not necessarily, an absorption measurement, a photoluminescence measurement, or a chemiluminescence measurement. Furthermore, the invention relates to an optical apparatus comprising a lens and reflector unit of said kind.

BACKGROUND

Changing the propagation path of a beam of optical radiation is a basic task for a large variety of optical applications. As an example we may consider the task in which light from a point-like source must be collimated, reflected to an angle, and focused into an image of said point-like source. This task is frequently encountered in such measurement devices where incident light from a light source is directed to a sample, and the optical emissions generated in the sample are measured and analyzed. In some applications a corresponding task only occurs in handling one of these directions, i.e. either the incident light or the optical emissions.

FIG. 1 illustrates schematically a known case in which a light source arrangement 101 comprises an essentially point-like light source (not separately shown). The emitted light is spatially limited so that what comes out of the light source arrangement 101 is an essentially conical beam of light. A first convex (or planoconvex, like in FIG. 1) lens 102 is used as a collimator that converts the diverging, conical beam of light into a cylindrical beam of collimated light. A mirror 103 reflects the cylindrical beam into a different direction. The angle 104 between the propagation direction of the incident beam and the propagation direction of the reflected beam is called the reflection angle. It is here 90 degrees but could as well be something else. The reflected beam passes through a second convex lens 105, which focuses it onto a target in an image arrangement 106, which is so called because if the focusing is appropriate, an image of the light source can be obtained in the image arrangement 106.

A drawback of the prior art arrangement of FIG. 1 is the relatively large number of optical material/surrounding material interfaces that the light must encounter on its path. Even in very high quality lenses some optical losses take place due to boundary reflections between the lens and the substance surrounding it. In lenses and mirrors also other optical effects take place, such as scattering, which all reduce the amount of transmitted light. Another drawback is related to the relative sensitivity to rough handling of a structure that has multiple separate optical elements that need to be accurately located and aligned.

FIG. 2 illustrates another prior art arrangement, in which the number of glass/air interfaces has been reduced from that of FIG. 1. The difference to FIG. 1 is the use of only one convex lens 202 between the light source arrangement 101 and the mirror 103. The focal length of lens 202 is selected so that the image of the light source is focused to the image arrangement 106. Drawbacks of this solution may include the increased distance needed between the light source arrangement 101 and the lens 202. Also the reflection coefficient from the mirror surface is significantly smaller than 1, whereas the total internal reflection corresponds to the reflection coefficient 1.

SUMMARY

An objective of the present invention is to present an optical element and an optical measurement apparatus in which the propagation of light is controlled with a small number of associated glass/air interfaces.

Another objective of the present invention is to present an optical element and an optical measurement apparatus that have a compact and robust structure.

Yet another objective of the present invention is to mitigate drawbacks of prior art solutions.

In accordance with a first aspect of the invention there is provided a lens and reflector unit for optical measurements, which includes:
  a first transparent body including
    a first convex surface section of said lens and reflector unit, said first convex surface section having a first central normal line,
    a second convex surface section of said lens and reflector unit, said second convex surface section having a second central normal line,
    a first flat surface section of said lens and reflector unit, said first flat surface section having a normal direction that divides an angle between said first and second central normal lines into equal halves; and
  a second transparent body including
    a third convex surface section of said lens and reflector unit, said third convex surface section having a third central normal line that intersects the second central normal line at a point that is also a focal point of a lens delimited by the second convex surface section and a plane that cuts the second convex surface section at its circumferential rim, and simultaneously intersects a focal point of a lens delimited by the third convex surface section and a plane that cuts the third convex surface section at its circumferential rim,
    a fourth convex surface section of said lens and reflector unit, said fourth convex surface section having a fourth central normal line, and
    a second flat surface section of said lens and reflector unit, said second flat surface section having a normal direction that divides an angle between said third and fourth central normal lines into to equal halves.

In accordance with a second aspect of the invention, there is provided an apparatus for performing optical emission analysis, which apparatus comprises
  a light source,
  a sample holder, and
  a detector;
and which is characterized in that the apparatus comprises a lens and reflector unit of the kind described above.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verb "to comprise" is used in this document as an open limitation that does not exclude the existence of also unrecited features. The features recited in depending claims are mutually freely combinable unless otherwise explicitly stated.

BRIEF DESCRIPTION OF THE FIGURES

The exemplifying embodiments of the invention and their advantages are explained in greater detail below in the sense of examples and with reference to the accompanying drawings, in which.

DESCRIPTION OF THE EMBODIMENTS

Figure 1:
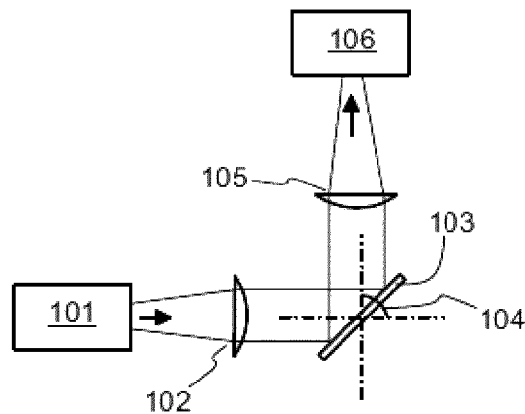
FIG. 1 illustrates an arrangement according to prior art.
Figure 2:
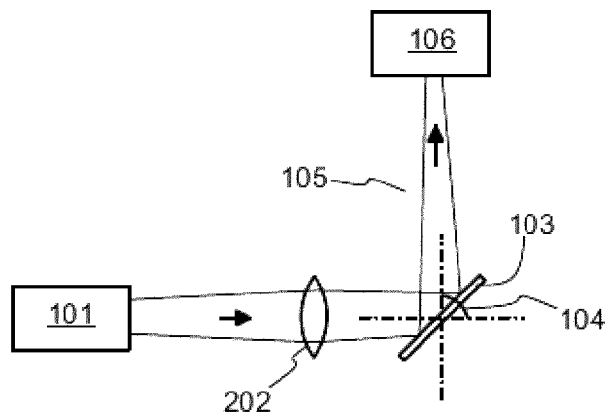
FIG. 2 illustrates another arrangement according to prior art.

FIGS. 1 and 2 have been discussed in the description of prior art.

Figure 3:
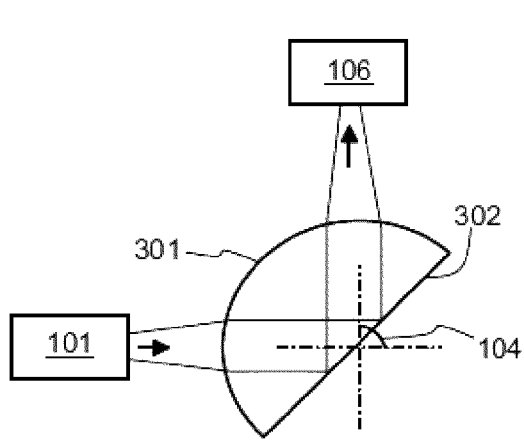
FIG. 3 illustrates the principle of a hemispherical lens according to prior art.

FIG. 3 illustrates a situation in which the light source arrangement 101 and the image arrangement 106 may resemble corresponding arrangements that are known from prior art. In the middle of the propagation path of the light is a hemispherical lens, the delimiting surfaces of which comprise an ellipsoidal surface 301 and a flat surface 302. In place of the ellipsoidal surface 301 there could be a (hemi)spherical surface (which actually is just a specific case of ellipsoidal surfaces) or an aspherically curved surface that is not ellipsoidal. The diverging conical beam of light emitted by the light source arrangement 101 enters the hemispherical lens through a first convex surface section that constitutes a portion of the ellipsoidal surface 301. This geometry causes the originally conical beam of light to be collimated into a beam with an unambiguous propagation direction. This collimated beam of light propagates inside the hemispherical lens up to the flat surface 302, which acts as a reflector and reflects the light into a reflection angle 104. Again in this particular example the reflection angle 104 is essentially 90 degrees, but this is an example only and does not limit the applicability of the invention(s) described in this text to also other magnitudes of reflection angles. Depending on the optical parameters and the material characteristics, the reflection at the flat surface may be an internal total reflection or an assisted reflection in which a reflective coating on the flat surface 302 (not separately shown) has a role.

Because the reflection takes place at a flat surface, the reflected beam is still a collimated beam of light with an unambiguous propagation direction. It exits the hemispherical lens through a second convex surface section that constitutes a portion of the ellipsoidal surface 301. This geometry causes the collimated beam to be focused into a converging conical beam that is focused into a focal point (not separately shown) in the image arrangement 106. It is easy to see that there are only two air-to-glass or glass-to-air interfaces that the light must pass through on its way between the light source arrangement 101 and the image arrangement 106.

Figure 4:
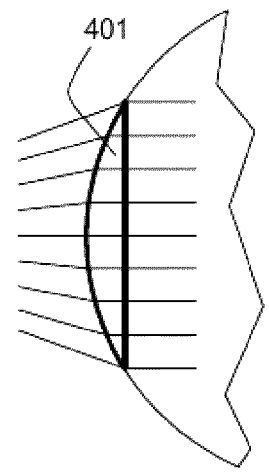
FIG. 4 illustrates a detail of the hemispherical lens of FIG. 3.

A hemispherical lens as such is known e.g. from the patent publication U.S. Pat. No. 5,682,449. FIG. 4 illustrates how the ellipsoidal segment of first convex surface section, at which the light beam meets the surface, covers a portion 401 of the hemispherical lens. As a hypothetical other delimiting surface of the portion 401 we may consider a plane that cuts the ellipsoidal surface of the hemispherical lens along a curve that is not smaller than and does not go inside of the outer circumference of the light beam. It is easy to see that the portion 401 acts just like a regular planoconvex lens. The hypothetical interface between this planoconvex lens and the remaining internal part of the hemispherical lens is a plane with exactly the same index of refraction on its both sides, so it does not affect the propagation of light inside the hemispherical lens. Consequently, when the exact form of a basic hemispherical lens is designed for a particular purpose, it is sufficient to consider the optical parameters of the lens material as well as the geometric properties of the ellipsoidal surface in that portion at which the light beam meets said ellipsoidal surface. Due to the planoconvex lens analogy it is within the capability of the person skilled in the art to design a hemispherical lens that has the necessary collimating and/or focusing characteristics.

Figure 5:
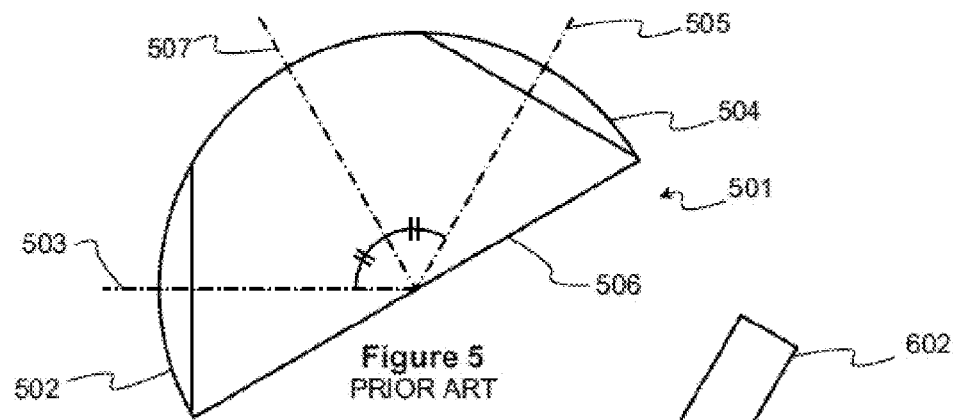
FIG. 5 illustrates some known concepts of optics used for explaining embodiments of the invention.

FIG. 5 illustrates in more detail certain known concepts that are useful in understanding embodiments of the invention. For changing the propagation path of a beam of optical radiation there is used a lens and reflector unit 501 made of material transparent to optical radiation. A first convex surface section 502 of the lens and reflector unit 501 has a first central normal line 503, which could be called the optical axis of the first convex surface section 502. A second convex surface section 504 of the lens and reflector unit 501 has a second central normal line 505, which could be called the optical axis of the second convex surface section 504.

Another delimiting surface of the lens and reflector unit 501 comprises a first flat surface section 506. A normal direction 507 of the first flat surface section 506, drawn at the point at which the first central normal line 503 and the second central normal line 505 meet the plane defined by the first flat surface section 506, divides the angle between the first central normal line 503 and the second central normal line 505 into equal halves. In this case, the lens and reflector unit 501 is a single transparent body. The first convex surface section, the second convex surface section and the first flat surface section are surface sections of the transparent body. Moreover, the first and second convex surface sections are parts of a common spherical or aspherically curved surface section that delimits said transparent body, which means that a spherical or aspherically curved delimiting surface of the transparent body continues smoothly from the first convex surface section to the second convex surface section.

Figure 6:
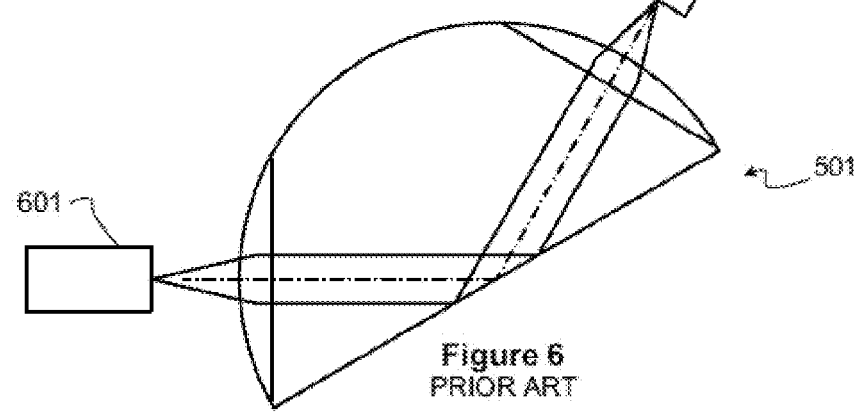
FIG. 6 illustrates an apparatus for performing optical emission analysis according to prior art.

In measurement apparatus applications it is typically necessary to not only direct incident light from a light source into a first focal point on a sample but to also collect emitted light from the sample into a second focal point from which it is taken to analysis. FIG. 6 illustrates an arrangement, in which two-way propagation of light through a lens and reflector unit 501 like that of FIG. 5 is utilized. The arrangement a schematic illustration of an exemplary apparatus for performing optical emission analysis. It comprises a light source 601, a sample holder 602 and a detector, which in this case is located at the same place as the light source 601. The detector may be for example a radiation detector or the receiving end of an optical fiber that is configured to conduct all received light to a detector located at another part of the apparatus.

The light source 601 is configured to emit a beam of incident light towards the lens and reflector unit 501. An axis of the beam of incident light is coincident with the line that was designated as the first central normal line 503 above in FIG. 5. As a result of the collimation, reflection and focusing effects explained earlier, what the sample holder 602 receives from the lens and reflector unit 501 is a beam of reflected incident light. An axis of said beam of reflected incident light is coincident with the line that was designated as the second central normal line 505 above in FIG. 5.

The optical emissions that the incident light causes in the sample are received through the same route through which the incident light propagated. We may nevertheless say that the beam of emitted light is directed into the lens and reflector unit 501 through a third convex surface section, which in this case only happens to be the same as the second convex surface section. Thus also its central normal line, designated here conceptually as the third central normal line, coincides with the second central normal line introduced above. Still for said reasons of consistency, we may say that the detector is configured to receive a beam of reflected emitted light from said lens and reflector unit, and that an axis of said beam of reflected emitted light is coincident with a fourth central normal line, which here happens to coincide with the first central normal line discussed above.

The optical emissions will typically come on a different wavelength than that of the incident light. If necessary, dichroic filters may be used at one or more locations in the arrangement to keep incident light from mixing with optical emissions from the sample.

Figure 7:
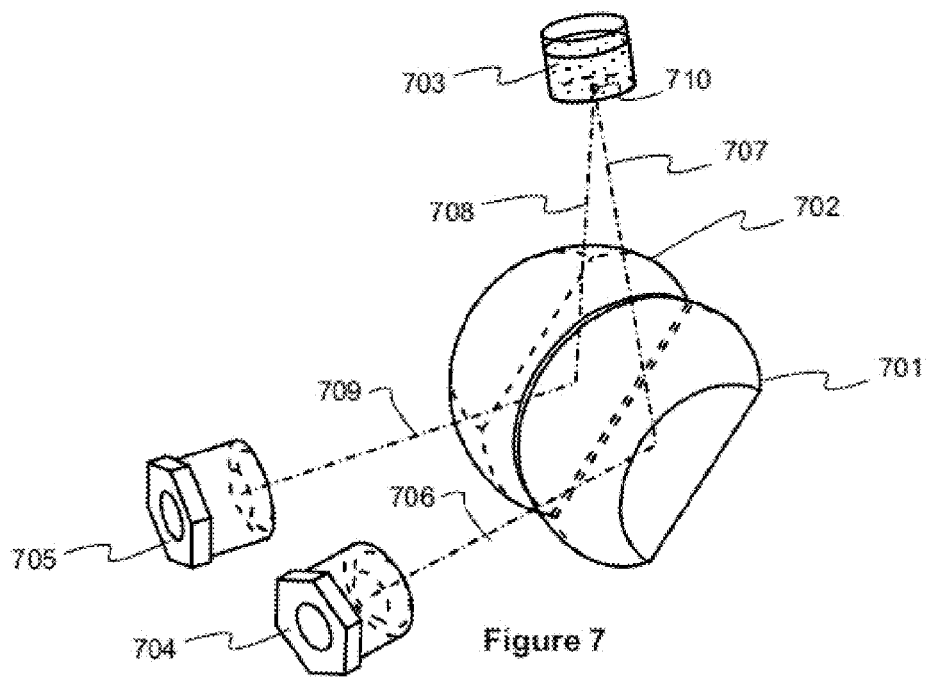
FIG. 7 illustrates an apparatus according to an embodiment of the invention for performing optical emission analysis.

FIG. 7 illustrates an apparatus according to an embodiment of the invention, in which the separation of incident light and optical emissions is more thorough in the sense that emitted light from the sample propagates to the detector along a path that is spatially different from the path of the incident light from the light source to the sample. In this case the lens and reflector unit comprises a first transparent body 701 and a second transparent body 702, each of which has the general appearance of a hemispherical lens. Of the concepts introduced above, the first convex surface section, the second convex surface section and the first flat surface section are surface sections of the first transparent body 701. The third convex surface section, the fourth convex surface section, and a second flat surface section are surface sections of the second transparent body 702.

It is evident that the lens and reflector unit of FIG. 7 does not need to consist of two mechanically separate pieces of transparent material. A lens and reflector unit with otherwise similar characteristics could be manufactured of a unitary piece as well.

The surfaces that delimit the first transparent body 701 are a flat bottom, an ellipsoidal surface, and two flat side surfaces. The first and second convex surface sections named above are parts of the ellipsoidal surface that delimits the first transparent body. Similarly the second transparent body 702 is delimited by a flat bottom, an ellipsoidal surface, and two flat side surfaces. The third and fourth con-vex surface sections named above are parts of the ellipsoidal surface that delimits the second transparent body. As was also explained above already in association with FIG. 3, whether or not a reflective coating is needed on the flat bottom surfaces depends on whether the reflection angles, optical material characteristics, and other applicable factors support utilizing the natural occurrence of an internal total reflection at the flat bottom surfaces.

Figure 8:
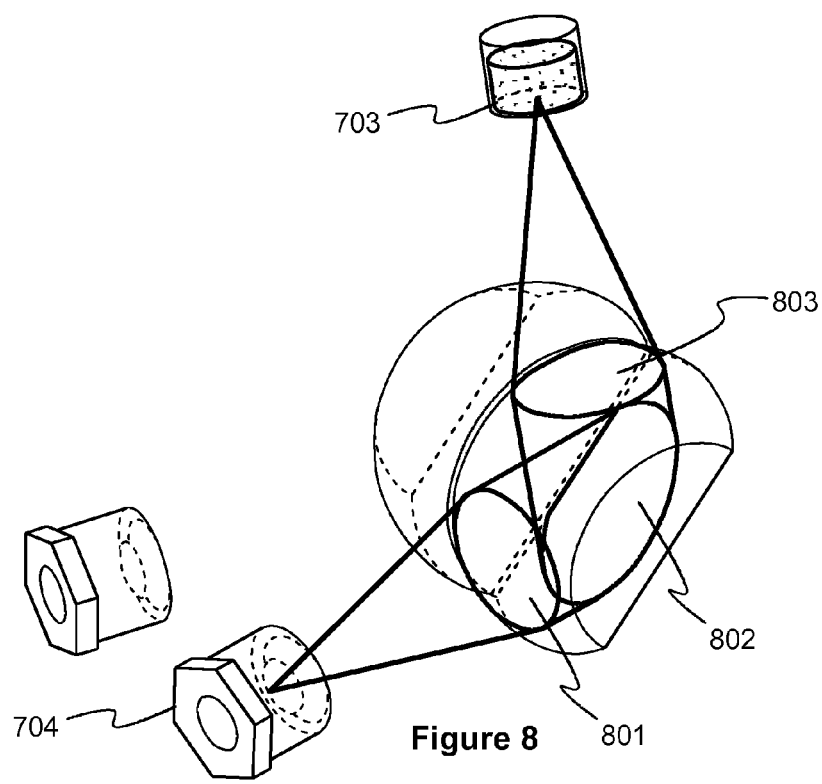
FIG. 8 illustrates the propagation of incident light in the apparatus of FIG. 7.

For holding the sample the apparatus comprises a sample well 703. A point-like source of incident light is conceptually located inside a first optical interface 704, while a second optical interface 705 represents the image arrangement at which the collected emitted light from the sample is to be focused. The paths of incident and emitted light are illustrated by showing the beam axes, which are coincident with the first central normal line 706 and the second central normal line 707 (for incident light) and the third central normal line 708 and the fourth central normal line 709 (for emitted light). The orientation of the reflecting flat surface sections is selected so that the second central normal line 707 and the third central normal line 708 intersect at a point 710 that is also a focal point of a lens formed by that part of the first transparent body that is delimited by the second convex surface section and a (hypothetical) plane that cuts said second convex surface section at its circumferential rim. Said point 710 is simultaneously a focal point of a lens formed by that part of the second transparent body that is delimited by the third convex surface section and a (hypothetical) plane that cuts said third convex surface section at its circumferential rim FIG. 8 illustrates in more detail the propagation of incident light. The diverging conical beam of incident light propagates from the light source in the first optical interface 704 through the first convex surface section 801, is reflected at the first flat surface section 802, and passes through the second convex surface section 803 from which it is focused into the focal point at the sample well 703.

Figure 9:
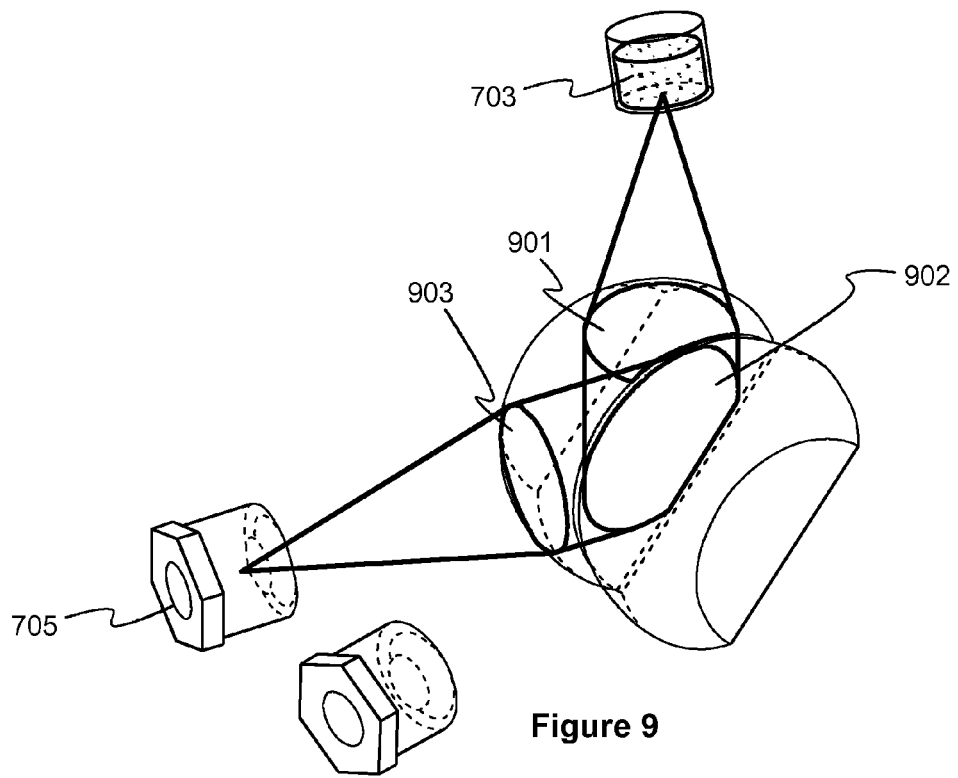
FIG. 9 illustrates the propagation of emitted light in the apparatus of FIG. 7.

FIG. 9 illustrates in more detail the propagation of emitted light. The diverging conical beam of emitted light propagates from the sample in the sample well 703 through the third convex surface section 901, is reflected at the second flat surface section 902, and passes through the fourth convex surface section 903 from which it is focused into a focal point at the second optical interface 705.

Figure 10:
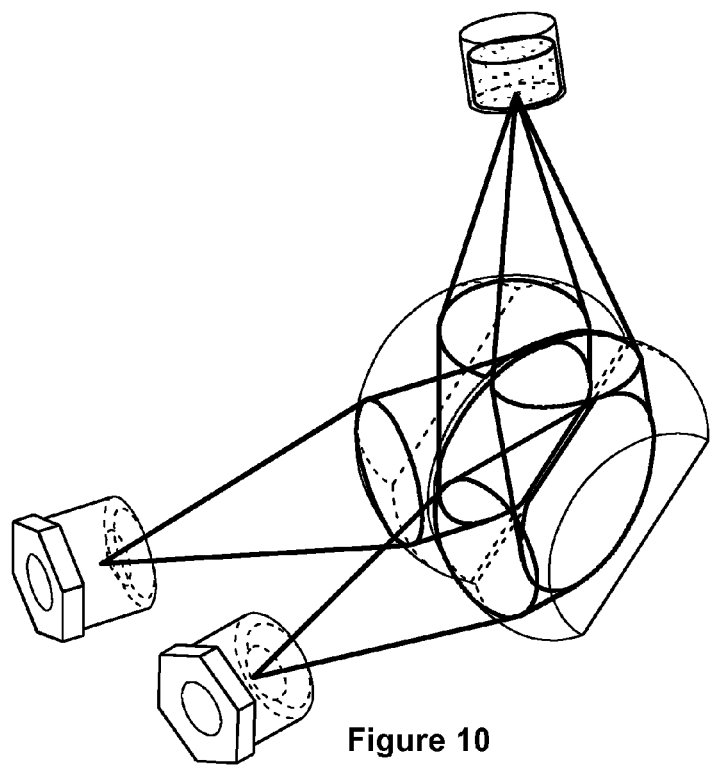
FIG. 10 illustrates both incident and emitted light in the apparatus of FIG. 7.

The tasks of illuminating the sample with incident light and collecting the emitted light from the sample may be performed at different times or simultaneously. FIG. 10 illustrates in a single picture the propagation of both the incident light and the emitted light.

Figure 11:
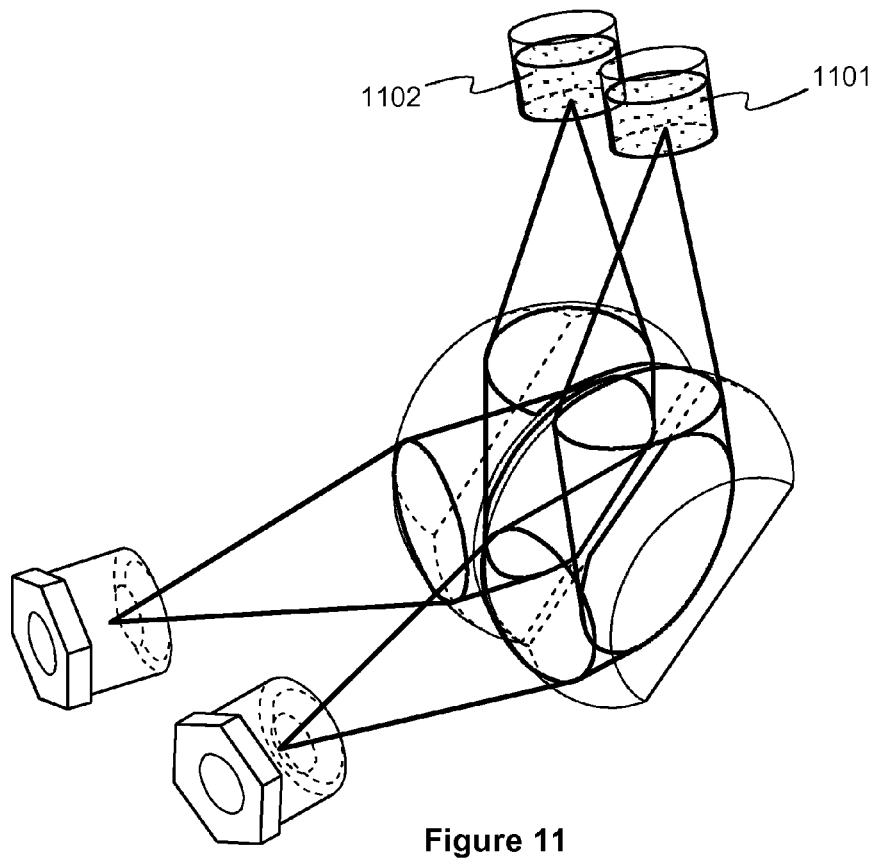
FIG. 11 illustrates another apparatus according to an embodiment of the invention for performing optical emission analysis.

By changing the orientation of the first and second transparent bodies it is possible to apply a relatively similar principle to a measurement in which a first sample is illuminated with incident light at the same time (or at least with unchanged mutual mechanical relations of the parts) when emitted light from a second, previously illuminated sample is collected and measured. A geometrically very similar solution may result if an embodiment of the invention is used to only collect emitted light, assuming that the necessary excitation of the sample to trigger the emission of detectable light has been accomplished in some other way. FIG. 11 shows such an embodiment of the invention, in which the first and second transparent bodies have been turned slightly apart, so that those of the previously named central normal directions that point towards the sample do not intersect at the focal point. A first sample well 1101 is located at the focal point of the lens portion that produces the focused incident light, while a second sample well 1102 is located at the focal point of the lens portion that collects the emitted light from the sample.

Figure 12:
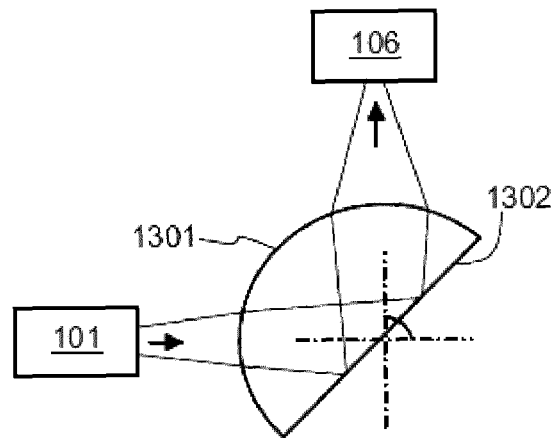
FIG. 12 illustrates known non-collimated propagation of light inside a lens and reflector unit.

The invention does not require that light should propagate inside the hemispherical lens only in collimated form. FIG. 12 illustrates an example which is according to the prior art but which is applicable in conjunction with embodiments of the invention. In this example, the lens and reflector unit is delimited by an ellipsoidal surface 1301 and a flat surface 1302. The light source 101 is closer to the first convex surface section, through which light enters the lens and reflector unit, than the focal point of the lens defined by said first convex surface section. As a result, the light beam that propagates inside the lens and reflector unit is still a slightly diverging conical beam. In another alternative example, which is applicable in conjunction with embodiments of the invention and which is not shown here, it could be a converging conical beam. If the point-like light source is located along the continuation of the central normal line of the first convex surface section, the axial direction of a diverging or converging conical beam inside the lens and reflector unit is still aligned with said central normal line. Thus all the considerations made so far about the mutual directions of the normal lines still hold.

Figure 13:
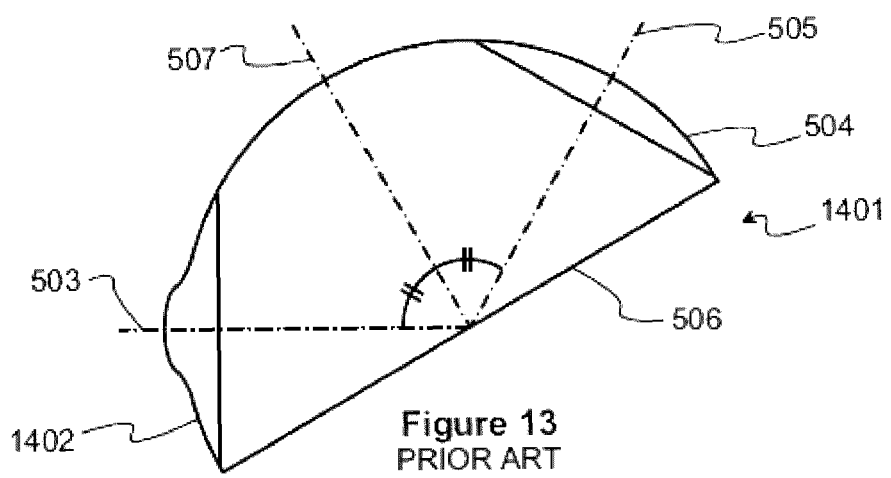
FIG. 13 illustrates a known lens and reflector unit with an aspherical convex surface section.

Additionally it should be noted that the invention does not exclude aspherical lens forms as parts of the convex surface sections that delimit the lens and reflector unit at those locations where light passes through. FIG. 13 illustrates an example which is according to the prior art but which is applicable in conjunction with embodiments of the present invention. In this example, the lens and reflector unit 1401 is otherwise similar than that illustrated earlier in FIG. 5, but it has an aspherical surface as the first convex surface section 1402.

Only advantageous exemplary embodiments of the invention are described in the figures. It is clear to a person skilled in the art that the invention is not restricted only to the examples presented above, but the invention may vary within the limits of the claims presented hereafter. Some possible embodiments of the invention are described in the dependent claims, and they are not to be considered to restrict the scope of protection of the invention as such. For example, although the description concentrates on embodiments in which the convex surface sections are parts of a common ellipsoidal or spherical surface, it is naturally possible to separately create an individual lens-like bulging portion or flat, reflective portion at each appropriate location of an otherwise even quite irregularly shaped piece of transparent material. However, utilizing a common spherical or aspherically curved surface has certain advantages in production due to the regularity of the overall form.

What is claimed is:

1. A lens and reflector unit for optical measurements, comprising:
   a first transparent body including
      a first convex surface section of said lens and reflector unit, said first convex surface section having a first central normal line,
      a second convex surface section of said lens and reflector unit, said second convex surface section having a second central normal line, and
      a first flat surface section of said lens and reflector unit, said first flat surface section having a normal direction that divides an angle between said first and second central normal lines into equal halves; and
   a second transparent body including
      a third convex surface section of said lens and reflector unit, said third convex surface section having a third central normal line that intersects said second central normal line at a point that is also a focal point of a lens delimited by said second convex surface section and a plane that cuts said second convex surface section at its circumferential rim, and simultaneously a focal point of a lens delimited by said third convex surface section and a plane that cuts said third convex surface section at its circumferential rim;
      a fourth convex surface section of said lens and reflector unit, said fourth convex surface section having a fourth central normal line; and
      a second flat surface section of said lens and reflector unit, said second flat surface section having a normal direction that divides an angle between said third and fourth central normal lines into equal halves.

2. The lens and reflector unit according to claim 1, wherein said first and second convex surface sections are parts of a common spherical or aspherically curved surface section that delimits said first transparent body, and
   said third and fourth convex surface sections are parts of a common spherical or aspherically curved surface section that delimits said second transparent body.

3. An apparatus for performing optical emission analysis, comprising
   a light source;
   a sample holder;
   a detector; and
   the lens and reflector unit according to claim 1.

4. The apparatus according to claim 3,
   wherein the light source is configured to emit a beam of incident light towards said lens and reflector unit, an axis of said beam of incident light being coincident with said first central normal line,
   the sample holder is configured to receive a beam of reflected incident light from said lens and reflector unit, and axis of said beam of reflected incident light being coincident with said second central normal line,
   the sample holder is configured to direct a beam of emitted light from a sample held in the sample holder towards said lens and reflector unit, an axis of said beam of emitted light being coincident with said third central normal line, and
   the detector is configured to receive a beam of reflected emitted light from said lens and reflector unit, and axis of said beam of reflected emitted light being coincident with said fourth central normal line.

5. The apparatus according to claim 3, wherein the sample holder is a part of a sample holding arrangement that is configured to controllably change the spatial relationship between the lens and reflector unit and a multitude of samples.

6. The apparatus according to claim 3, further comprising:
   a first optical interface, which is the light source;
   a second optical interface adjacent to the first optical interface, the second optical interface being the detector in the form of one of a radiation detector and a receiving end of an optical fiber that is configured to conduct all received light to a radiation detector located at another part of the apparatus,
   at least one sample well for holding a sample,
   wherein the first transparent body is configured to receive light from said first optical interface in a direction defined by said first central normal line, and to direct light into said sample well in a direction defined by said second central normal line, and
   the second transparent body is configured to receive light from said sample well in a direction defined by said third central normal line, and to direct light into said second optical interface in a direction defined by said fourth central normal line.

7. The apparatus according to claim 4, wherein the sample holder is a part of a sample holding arrangement that is configured to controllably change the spatial relationship between the lens and reflector unit and a multitude of samples.

8. The apparatus according to claim 4, further comprising:
a first optical interface, which is the light source;
a second optical interface adjacent to the first optical interface, the second optical interface being the detector in the form of one of a radiation detector and a receiving end of an optical fiber that is configured to conduct all received light to a radiation detector located at another part of the apparatus,
at least one sample well for holding a sample,
wherein the first transparent body is configured to receive light from said first optical interface in a direction defined by said first central normal line, and to direct light into said sample well in a direction defined by said second central normal line, and
the second transparent body is configured to receive light from said sample well in a direction defined by said third central normal line, and to direct light into said second optical interface in a direction defined by said fourth central normal line.

9. The apparatus according to claim 5, further comprising:
a first optical interface, which is the light source;
a second optical interface adjacent to the first optical interface, the second optical interface being the detector in the form of one of a radiation detector and a receiving end of an optical fiber that is configured to conduct all received light to a radiation detector located at another part of the apparatus,
at least one sample well for holding a sample,
wherein the first transparent body is configured to receive light from said first optical interface in a direction defined by said first central normal line, and to direct light into said sample well in a direction defined by said second central normal line, and
the second transparent body is configured to receive light from said sample well in a direction defined by said third central normal line, and to direct light into said second optical interface in a direction defined by said fourth central normal line.

* * * * *